United States Patent [19]

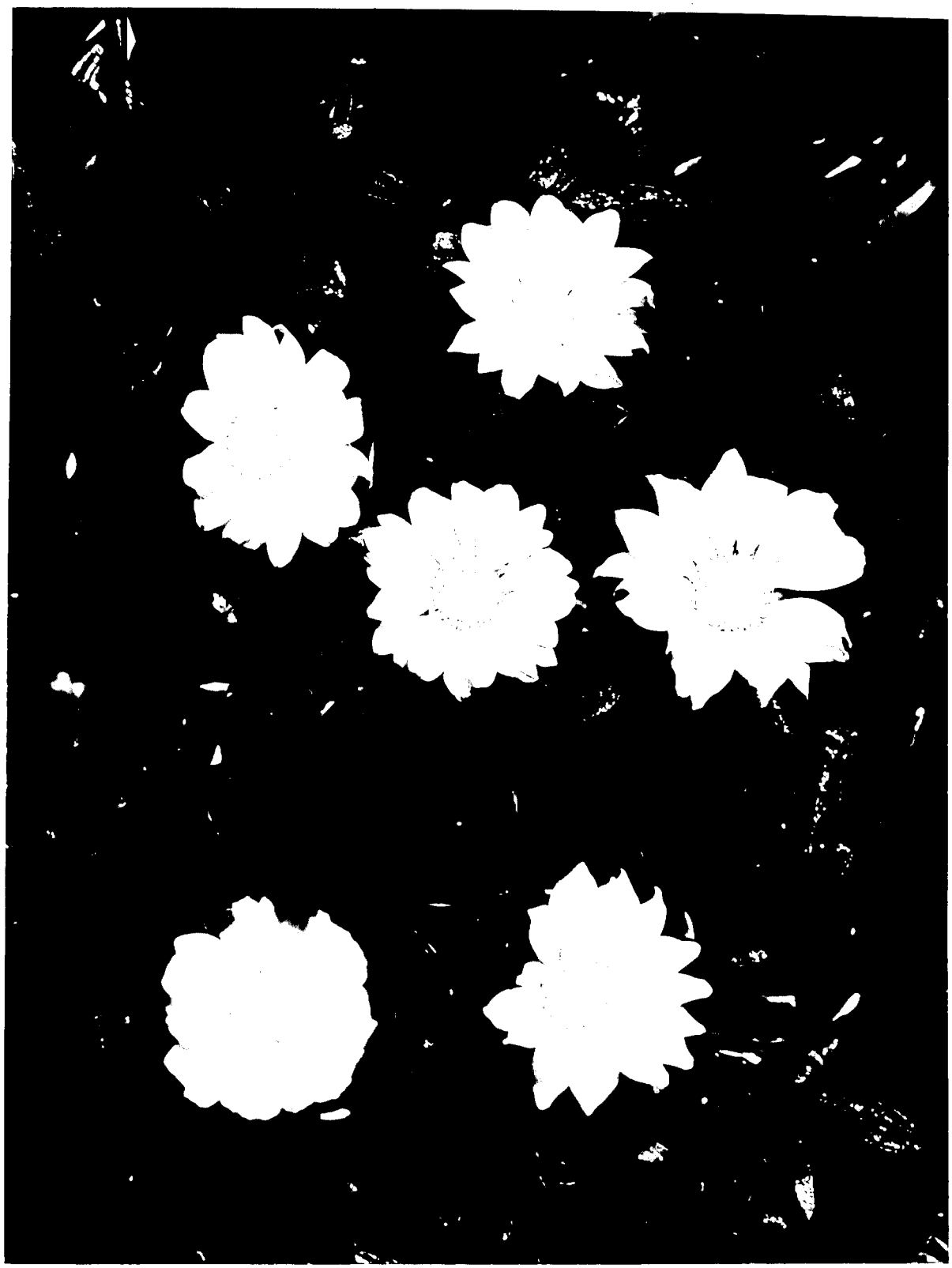

Beimel

[11] Patent Number: Plant 5,797

[45] Date of Patent: Nov. 4, 1986

[54] GAZANIA PLANT CALLED MITSUWA WHITE

[75] Inventor: Stephen H. Beimel, Agoura, Calif.

[73] Assignee: Mitsuwa Nursery, Inc., Moorpark, Calif.

[21] Appl. No.: 777,281

[22] Filed: Sep. 18, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Roylance, Abrams, Berdo & Goodman

[57] ABSTRACT

A Gazania named Mitsuwa White having pure white flowers with a yellow center which is easier to propagate as compared to other trailing Gazanias, and which is very consistent as to color in successive propagations. The foliage is noteworthy for having two characteristics not often found together in Gazanias; dark green leaves and a full trailing habit.

1 Drawing Figure

BACKGROUND OF THE INVENTION

The present invention relates to a new and distinctive cultivar of Gazania plant botanically known as *Gazania rigens* Mitsuwa White, and referred to commercially by the cultivar name "Mitsuwa White".

"Rigens" is the Latin botanical name given by the County Arboretum of Los Angeles, Calif. to the first of the Mitsuwa gazanias called Mitsuwa Yellow, (registered trademark). Mitsuwa Yellow is commercially well known. Mitsuwa White is smiliar in appearance and growing habits to Mitsuwa Yellow, except for the substantial difference in the color of the flowers, i.e., the bright yellow of the parent Mitsuwa Yellow as compared to the pure white with the yellow center spot of Mitsuwa White.

BRIEF DESCRIPTION OF THE INVENTION

Gazanias, in general, are a genus of herbs of the aster family which are characterized by large, showy, orange and yellow blossoms and which prefer bright sunshine. They are native to South Africa but are now widely cultivated and are commercially important. Gazanias were named after Theodorus Gaza, a medieval Greek scholar of Italy.

DESCRIPTION OF THE DRAWING

The accompanying color photograph, forming a part of this disclosure, was taken in March of 1985 in Moorpark, Calif., and shows Mitsuwa White growing in a bed; the view being more or less looking straight down onto the plant. The photograph shows the colors of all parts of Mitsuwa White as true as is reasonably possible in this type of color photograph.

DETAILED DESCRIPTION

Mitsuwa White is a spontaneous sport or mutant discovered by Mr. Stephen H. Beimel in the nursery of Mitsuwa Nursery, Inc. of Moorpark, Calif..

Asexual reproduction, starting by propagating cuttings from the originally discovered sport, has reproduced the unique features of this new plant through successive propagations. Crown cuttings (a major stem with several leaves) were used for this propagation. Mitsuwa White is distinguished from its parent and from all other commercial Gazanias in general by several characteristics.

The color of the flowers of Mitsuwa White is very consistent. This of course makes it highly desirable to consumers and thus commercially valuable. With virtually all other commercially available varieties of Gazanias there is at least some tendency to produce sports which are undesirable in that such sports display a substantial variance from true in shape, size and color of the flowers.

Mitsuwa White is a "sister" sport of another Gazania called Mitsuwa Orange. Mitsuwa Orange is the subject of a copending U.S. plant patent application filed by Toshiaki Ono, and commonly owned with this application by Mitsuwa Nursery, Inc. Mitsuwa Orange and Mitsuwa White, except for the dramatic difference in the colors of their flowers, are very similar to each other in all other ways.

The Mitsuwa Whie plant and foliage in common with Mitsuwa Orange, has a double thrust improvement over a known existing variety of orange gazania. That prior plant is, botanically, *Gazania uniflora leucoleana,* and is known commonly as orange trailing gazania.

However, Mitsuwa White, as compared to this prior known plant, has dark green leaves and has a full trailing (spreading) habit. The prior plant has silver grey colored leaves, and has only a semi-trailing habit. Further, the leaves of Mitsuwa White are not only this richer dark green color but are also relatively wider.

There are other known gazanias that have dark green leaves, but these do not have a full trailing habit. There are other known Gazanias that have a full trailing habit but do not have dark green leaves. Mitsuwa Orange and Mitsuwa White are the only known gazanias to have both these desirable characteristics of dark green leaves and a full trailing habit.

Mitsuwa White, in the climate of southern California, in common with most other gazanias, blooms nearly all year long.

Mitsuwa White is much easier to propagate than *Gazania uniflora leucoleana.* More specifically, the time needed to produce a root system for Mitsuwa White is about 40% less than the time needed to produce a root system for *Gazania uniflora leucoleana.*

Color references herein, except where the ordinary dictionary meaning is clear from the context, are to The Royal Horticultural Colour Chart. The following characterizations were made by the discoverer and other personnel of Mitsuwa Nursery, Inc., based on the flowers shown in the photograph herein.

Flower, petal upside, White 155D

Flower, petal downside, White 155A

Leaves, upside, Green 137A

Leaves, downside, White 155D

As shown in the photograph, Mitsuwa White also features a gradation of the yellow center outwardly along the white petals which further distinguishes Mitsuwa White from its Mitsuwa Yellow parent and from Mitsuwa Orange.

Mitsuwa White is a fine ground cover. In the southern California climate it has been found to be commercially valuable as a relatively inexpensive and efficient substitute for certain annual flowering plants. Mitsuwa White has been found to bloom more heavily in summer than its parent Mitsuwa Yellow.

The buds display the characteristic roughly acorn shape common to Gazanias.

I claim:

1. A new and distinct cultivar of Gazania named Mitsuwa White, as described and illustrated, and particularly characterized by its pure white flowers having a yellow center and its dark green foliage having a full trailing habit.

* * * * *